US010119961B2

(12) United States Patent
Freeby et al.

(10) Patent No.: US 10,119,961 B2
(45) Date of Patent: *Nov. 6, 2018

(54) STAIN-FREE PROTEIN QUANTIFICATION AND NORMALIZATION

(71) Applicant: Bio-Rad Laboratories, Inc., Hercules, CA (US)

(72) Inventors: Steve Freeby, Vacaville, CA (US); Ning Liu, Fremont, CA (US); Kevin McDonald, Novato, CA (US); Aran Paulus, San Jose, CA (US); Anton Posch, Grafing (DE)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/293,154

(22) Filed: Oct. 13, 2016

(65) Prior Publication Data

US 2017/0030922 A1     Feb. 2, 2017

Related U.S. Application Data

(63) Continuation of application No. 13/870,710, filed on Apr. 25, 2013, now Pat. No. 9,606,111.

(60) Provisional application No. 61/639,692, filed on Apr. 27, 2012, provisional application No. 61/639,686, filed on Apr. 27, 2012.

(51) Int. Cl.
| | |
|---|---|
| *G01N 33/53* | (2006.01) |
| *G01N 33/68* | (2006.01) |
| *G06F 19/10* | (2011.01) |
| *G06T 7/00* | (2017.01) |
| *G06T 11/60* | (2006.01) |

(52) U.S. Cl.
CPC ......... *G01N 33/53* (2013.01); *G01N 33/6827* (2013.01); *G06F 19/10* (2013.01); *G06T 7/0012* (2013.01); *G06T 11/60* (2013.01); *G06T 2207/30004* (2013.01)

(58) Field of Classification Search
CPC .... G01N 33/53; G01N 33/6827; G06F 19/10; G06T 7/0012
See application file for complete search history.

(56) References Cited

U.S. PATENT DOCUMENTS

| | | | |
|---|---|---|---|
| 6,873,914 B2 | 3/2005 | Winfield et al. | |
| 7,224,826 B2 | 5/2007 | Shibazaki et al. | |
| 7,433,035 B2 | 10/2008 | Gorelik et al. | |
| 7,569,130 B2 | 8/2009 | Edwards et al. | |
| 7,635,598 B2 | 12/2009 | Cook et al. | |
| 7,741,046 B2 | 6/2010 | Larsen et al. | |
| 8,007,646 B2 | 8/2011 | Edwards et al. | |
| 2004/0176922 A1 | 9/2004 | Samsoondar | |
| 2011/0306514 A1 | 12/2011 | Hewitt et al. | |
| 2012/0045848 A1 | 2/2012 | Haugland et al. | |

FOREIGN PATENT DOCUMENTS

| | | | |
|---|---|---|---|
| WO | 00-63683 A1 | 10/2000 | |
| WO | WO-2010083252 A2 * | 7/2010 | ....... G01N 33/57484 |
| WO | 2014/004959 A1 | 1/2014 | |

OTHER PUBLICATIONS

"Research Papers Using Stain-Free Technology as Loading Controls in Western Blots." Bio-Rad Bulletin 6351 Rev A. Copyright 2013.
Aldridge GM et al. "The use of total protein stains as loading controls: an alternative to high-abundance single-protein controls in semi-quantitative immunoblotting." *J. Neurosci. Methods* 172, 250-254, 2008.
Colella AD et al. "Comparison of Stain-Free gels with traditional immunoblot loading control methodology." *Anal. Biochem.* 430, 108-110, 2012.
Cully TR et al. "Changes in plasma membrane Ca-ATPase and stromal interacting molecule 1 expression levels for Ca(2+) signaling in dystrophic mdx mouse muscle." *Am J Physiol Cell Physiol.* 303, C567-76, 2012.
Dittmer A and Dittmer J. "β-actin is not a reliable loading control in Western blot analysis." *Electrophoresis* 27, 2844-2845, 2006.
Dutka TL et al. "Effects of carnosine on contractile apparatus $Ca^{2+}$ sensitivity and sarcoplasmic reticulum $Ca^{2+}$ release in human skeletal muscle fibers." *Journal of Applied Physiology* 112, 728-736, 2012.
Dvortsov IA et al. "Ethidium bromide is good not only for staining of nucleic acids but also for staining of proteins after polyacrylamide gel soaking in trichloroacetic acid solution." *Anal. Biochem.* 353, 293-295, 2006.

(Continued)

*Primary Examiner* — Paul J Holland
(74) *Attorney, Agent, or Firm* — Kilpatrick, Townsend and Stockton LLP (57) ABSTRACT

Disclosed herein are methods of protein quantification and normalization using haloalkylated tryptophan fluorescence. Complex protein samples, i.e., samples that each contain 1,000 or more distinct proteins, from diverse sources that do not have common protein profiles are treated with a halo-substituted organic compound (i.e. haloalkane) that reacts with tryptophan residues to form fluorescent products. Irradiation of the samples with ultraviolet light and the detection and quantification of the resultant fluorescent emissions from all proteins in each sample are then used to obtain comparative values for total protein content among the various samples. The values thus obtained are found to be valid indications of comparative total protein content, despite the fact that the tryptophan levels vary widely among the various proteins in any single sample and the samples, due to the diversity of their origins, tend to differ among themselves in the identities and relative amounts of the proteins that they contain. Protein samples are also normalized to correct for differences in sample dilution, sample loading, and protein transfer inconsistencies, by using stain-free detection of total protein in each of the samples, or detection of subsamples within each sample.

11 Claims, 6 Drawing Sheets

(56) References Cited

OTHER PUBLICATIONS

Edwards RA et al. "The light-induced reactions of tryptophan with halocompounds." *Photochem. & Photobiol.* 75, 362-368, 2002.
Elbaggari A et al. "Evaluation of the Criterion Stain FreeTM gel imaging system for use in Western blotting applications." Bio-Rad Bulletin 5781 Rev A. Copyright 2008.
Elliott S et al. "Lack of expression and function of erythropoietin receptors in the kidney." *Nephrol. Dial. Transplant.* 27, 2733-2745, 2012. ePub Dec. 13, 2011.
Gürtler A et al. "Stain-Free technology as a normalization tool in Western blot analysis." *Anal. Biochem.* 433, 105-111, 2013. ePub Oct. 19, 2012.
Hammond M et al. "A method for greater reliability in Western blot loading controls: stain-free total protein quantitation". Bio-Rad Bulletin 6360. Copyright 2013.
Kazmin D et al. "Visualization of proteins in acrylamide gels using ultraviolet illumination." *Anal. Biochem.* 301, 91-96, 2002.
Ladner CL et al. "Development of indole chemistry to label tryptophan residues in protein for determination of tryptophan surface accessibility." *Protein Sci.* 16, 1204-1213, 2007.
Ladner CL et al. "Identification of trichloroethanol visualized proteins from two-dimensional polyacrylamide gels by mass spectroscopy." *Anal. Chem.* 78, 2388-2396, 2006.
Ladner CL et al. "Visible fluorescent detection of proteins in polyacrylamide gels without staining." *Anal. Biochem.* 326, 13-20, 2004.
Larkins NT et al. "Influences of temperature, oxidative stress, and phosphorylation on binding of heat shock proteins in skeletal muscle fibers." *Am J Physiol Cell Physiol* 303, C654-C665, 2012.
Li and Shen. "An old method facing a new challenge: Re-visiting housekeeping proteins as internal reference control for neuroscience research." *Life Sciences* 92, 747-751, 2013.
McDonald K et al. "In-Gel Protein Quantitation Using the Criterion Stain-Freer™ Gel Imaging System." Bio-Rad Bulletin 5782. Copyright 2008.
Mollica JP et al. "S-glutathionylation of troponin I (fast) increases contractile apparatus Ca2+ sensitivity in fast-twitch muscle fibres of rats and humans.". The Journal of Physiology 590, 1443-1463, 2012.
Murphy RM et al. "Ca2+-dependent proteolysis of junctophilin-1 and junctophilin-2 in skeletal and cardiac muscle." *The Journal of Physiology*, 591, 719-729, 2013.
Pinchuk SV and Vorobei AV. "Spectral characteristics and mechanisms of forming 'chloroform-dependent' tryptophan photoproducts." *J. Applied Spectroscopy* 59, 711-715, 1993.
Romero-Calvo I et al. "Reversible Ponceau staining as a loading control alternative to actin in Western blots." *Anal. Biochem.* 401, 318-320, 2010.
Short R and Posch A. Stain-Free Approach for Western Blotting: Alternative to the Standard Blot Normalization Process. Genetic Engineering and Biotechnology News vol. 31, No. 20. Nov. 15, 2011. http://www.genengnews.com/gen-articles/stain-free-approach-for-western-blotting/3920/.
Welinder C and Ekblad L. Coomassie Staining as Loading Control in Western Blot Analysis. *J. Proteome Res.* 10, 1416-1419, 2011.
Zhong H et al. "The heteromeric cyclic nucleotide-gated channel adopts a 3A:1B stoichiometry." *Nature* 420, 193-198, 2001.
The International Search Report and Written Opinion from PCT/US2013/038250, dated Sep. 18, 2013.
The European Search Report dated Nov. 27, 2015.

\* cited by examiner

STAIN-FREE PROTEIN QUANTIFICATION AND NORMALIZATION

CROSS-REFERENCES TO RELATED APPLICATIONS

The present application is a continuation of U.S. patent application Ser. No. 13/870,710, filed Apr. 25, 2013, now U.S. Pat. No. 9,606,111, issued Mar. 28, 2017, which claims priority from U.S. Provisional Application No. 61/639,692, entitled "Stain-free total protein quantification of complex samples from diverse sources" and filed Apr. 27, 2012, and U.S. Provisional Application No. 61/639,686, entitled "Stain-free technology for western blot total normalization" and filed Apr. 27, 2012, each of which are herein incorporated by reference for all purposes.

BACKGROUND OF THE INVENTION

Laboratory procedures in biotechnology frequently include the detection, identification, and quantitation of individual proteins. Certain procedures also however require the quantitation of entire mixtures of proteins aside from the individual proteins in each mixture, and with or without separating or differentiating the individual proteins from each other. Such total protein quantitation is of value, for example, when comparing protein amounts from different samples, including samples from different subjects, different organisms, and different species, or from the same species or subjects at different stages of development or different stages of disease or disease conditions. Total protein determinations in these cases can reveal quantitative changes in gene expression, which can be of value of diagnosis, treatment, and the testing of therapeutic agents. Total protein determinations can also be used to check sample loadings and protein transfers in analytical systems. When loading samples into individual wells of a microplate or individual lanes of an electrophoresis gel, for example, a uniform and consistent loading among the various wells or lanes is needed to assure that proper comparisons can be made in any of the separations or other procedures that might be performed on the samples. Protein transfers arise in Western blots, for example, which are also an area of concern, since total protein quantitations can indicate whether a blot has been performed correctly or an incomplete transfer has occurred.

Protein detections and quantitations using conventional stains such as COOMASSIE™ Brilliant Blue (BASF Aktiengesellschaft, Ludwigshafen, Germany), Ponceau S (Sigma-Aldrich, St. Louis, Mo., USA), and SYPRO RUBY™ (Sigma-Aldrich) are well known. A stain-free technique is disclosed by Edwards et al. in U.S. Pat. No. 7,569,103 B2 (Aug. 4, 2009) and U.S. Pat. No. 8,007,646 B2 (Aug. 30, 2011), citing the UV light-induced reaction between the indole moiety of tryptophan and any of various halo-substituted organic compounds, with specific mention of chloroform, trichloroethanol, and trichloroacetic acid, to produce a fluorescent compound with emissions at wavelengths in the visible range. The technique thus entails treating the proteins, or the gels in which the proteins reside, with the halogen-containing reagent, exposing the proteins or gels to UV light, and detecting and quantifying the resulting emission for individual protein bands.

Tryptophan is relatively rare in proteins, and the proportion of tryptophan residues to total amino acid residues within each protein varies widely from one protein to the next. For this reason, recognition of the usefulness of the stain-free technique to date has been limited. The technique is thus known to be useful for comparing different samples of the same protein, for example, by comparing the intensity of a single band of the same molecular weight protein in each sample. Comparisons between different protein bands in different samples would not be useful, since the different proteins are most likely to have different tryptophan contents and thus cannot be expected to produce the same signal intensities when present in the same amounts. The tryptophan variances do not necessarily limit the usefulness of the technique to the comparison of individual proteins, however. Total protein determinations are valid when performed on samples from the same source. The technique can be used in a blotting experiment for example for comparing the stain-free signal in a gel before and after blotting to determine if any protein has remained in the gel. The technique can also be used for absolute quantitation by creating a standard curve using a range of known concentrations of a protein and evaluating a sample containing an unknown amount of the same protein provided that the amount of the protein the sample is within the range of the standard curve. Nevertheless, in all cases the comparisons are direct comparisons either between the same sample before and after some form of manipulation, or of the same individual protein in different samples. In neither of these cases would any differences in tryptophan contents between different proteins negate the validity of the result.

When investigating an individual protein of interest a sample, it is sometimes beneficial to normalize the amount of that protein with respect to one or more other proteins in the sample, or with respect to all proteins in the sample. Normalization is a means to correct experimental data to accommodate for differences in sample dilution, sample loading, or protein transfer inconsistencies. For example, if two different cell cultures are used as samples it is likely that each culture contains different numbers of cells. If each cell in both samples has the same amount of a particular protein then the culture with more cells will have more of the protein. Without knowing that one sample contained more cells than the other one would incorrectly conclude that an average cell in one culture had more of the protein than an average cell in the other culture. One uses normalization to correct for this type of difference.

The most common normalization method is the use of housekeeping proteins (HKPs). In order to be considered a HKP a protein must be present in approximately the same quantity in all samples. Tubulin, GAPDH, and actin are frequently chosen as HKPs due to their general lack of variability associated with changes in experimental conditions. As a number of publications have shown, however, caution should be used when selecting HKPs since not all HKPs are constant under changes in experimental conditions or sample types. For this reason, it is often recommended that results are validated using multiple HKPs, adding time and complexity to western blot experiments.

The process of using HKPs for blot normalization can be daunting. Two frequently used techniques are "strip and reprobe" and multiplex fluorescent detection. Regardless of the method used, HKP-based normalization with GAPDH, actin or tubulin needs to be optimized for linear range of detection, antibody dilutions, incubation times and imaging settings.

Using the strip and reprobe method, the protein of interest is probed and detected. Antibodies and detection chemistries are then stripped from the membrane using some combination of heat, detergent, or reducing agent. The blot may then be re-probed with HKP specific antibody and re-detected.

Not only is the process time consuming, but inevitably, the stripping process will remove some level of antigen, thereby compromising downstream results.

Multiplex fluorescent western blotting is a more elegant solution, whereby multiple antigens can be simultaneously probed and detected using multiple fluorescently labeled secondary antibodies. Multiplex Western blotting requires the same optimizations as noted above, but has other challenges like antibody cross-reactivity, and should have an optimization process in place that validates the detection of each antigen separately, before attempting a multiplex detection.

If one wishes to avoid the challenges associated with the use of HKPs by stripping and reprobing, or with optimization of multiplex fluorescent blot detection, one can instead use a technique called total protein normalization (TPN). There are three commonly used methods for perform TPN. The first is to perform a protein assay on the samples prior to analysis and then to dilute them to the same concentration for the analysis. This is commonly done using a Bradford dye assay, a bicinchoninic acid (BCA) assay, or other similar methods. Unfortunately this method assumes that there is no variability within the process and this is not always the case. Any pipetting variation as samples are prepared and loaded onto the gel is not accounted for nor does this method account for variations in the blotting efficiency between the gel and the membrane. Another method of performing TPN is to stain the gel after it is run. This can be done using reversible stains such as zinc or copper based stains that bind to the proteins within the gel for detection yet can be washed away so as not to interfere with the blotting process and subsequent immunodetection. Although this method accounts for variations in the sample preparation and gel loading it does not account for blotting efficiency and it adds time and complexity to the process. The third method for performing TPN is to use colored or fluorescent stains on the membrane such as SYPRO Ruby, Ponceau S, and Amido Black. This method accounts for variability in sample preparation and transfer efficiency but it still adds time and complexity to the process.

The present invention provides a new and easier method, one that performs TPN by use of stain-free technology, thereby avoiding the difficulties associated with HKP and eliminating the drawbacks with existing TPN methods.

SUMMARY OF THE INVENTION

Provided herein are methods of using haloalkylated tryptophan fluorescence to quantify and compare the total amount(s) of protein in one or more target protein samples, and normalize the amount(s) of one or more proteins within or among protein samples.

In some embodiments, a method of quantifying the total amount of protein in a target protein sample using detected haloalkylated tryptophan fluorescence is provided. The method comprises, for each of a plurality of reference protein samples, providing the total amount of protein in the reference protein sample, and quantifying the amount of haloalkylated tryptophan fluorescence detected from the reference protein sample. The method further comprises quantifying the amount of haloalkyated tryptophan fluorescence detected from the target protein sample. In addition, the method comprises quantifying the total amount of protein in the target protein sample based upon the total amounts of protein in the reference protein samples and the amounts of haloalkylated tryptophan fluorescence detected from the reference protein samples and the target protein sample.

In one embodiment of this method, the total amount of protein in the target protein sample is quantified on a computer.

In another embodiment of the method, the target protein sample contains about 1,000 or more distinct proteins.

In yet another embodiment of the method, the target protein sample is obtained from a serum sample, tissue homogenate, or cell lysate.

In still another embodiment of the method, each reference protein sample contains about 1,000 or more distinct proteins.

In another embodiment of the method, at least one reference protein sample is obtained from a serum sample, tissue homogenate, or cell lysate.

In yet another embodiment of the method, at least two reference protein samples are obtained from different cells or tissues obtained from the same individual organism.

In still another embodiment of the method, at least two reference protein samples are obtained from different individual organisms of the same species.

In another embodiment of the method, at least two reference protein samples are obtained from different species.

In yet another embodiment of the method, the total amount of protein in at least one of the reference protein samples is provided from a spectrophotometric measurement.

In still other embodiments, the method further comprises the step of constructing a standard curve that quantitatively relates the total amount of protein to the amount of haloalkylated tryptophan fluorescence for the reference protein samples, and wherein the total amount of protein in the target protein sample is quantified using the standard curve. The total amount of protein in the target protein sample can be quantified by linear interpolation or linear extrapolation.

Also provided is a method of quantitatively comparing the relative total amounts of protein in two target protein samples using detected haloalkylated tryptophan fluorescence. The method comprises quantifying the amount of haloalkylated tryptophan fluorescence detected from each target protein sample; calculating the ratio of the amounts of haloalkylated tryptophan fluorescence detected from the target protein samples; and comparing the relative total amounts of protein in the target protein samples based upon the ratio.

In one embodiment of this method, the relative total amounts of protein in the target protein samples are compared on a computer.

In another embodiment of the method, the ratio of the amounts of haloalkylated tryptophan fluorescence detected from the target protein samples is interpreted as the ratio of the total amounts of protein in the target protein samples.

In yet another embodiment of the method, each target protein sample contains about 1,000 or more distinct proteins.

In still another embodiment of the method, each target protein sample is obtained from a serum sample, tissue homogenate, or cell lysate.

In any of the methods provided above, the amount of haloalkylated tryptophan fluorescence detected from each protein sample can be quantified by obtaining an image of a portion of an electrophoresis gel or blotting membrane, said portion comprising the protein sample, and determining the total amount of haloalkylated tryptophan fluorescence arising from the protein sample in the image. In some embodiments, the electrophoresis gel or blotting membrane comprises a plurality of lanes, and the portion of the electrophoresis gel or blotting membrane corresponds to one lane. In some embodiments, the image is obtained by contacting the protein sample with a haloalkane, exposing the electrophoresis gel or blotting membrane to UV light, and recording fluorescently re-emitted light having a wavelength of from about 400 nm to about 500 nm. The haloalkane can be selected from the group consisting of chloroform, trichloroacetic acid, and trichloroethanol.

In some embodiments of these methods, the total amount of haloalkylated tryptophan fluorescence arising from the protein sample in the image is determined by integrating the haloalkylated tryptophan fluorescence over the area of the image.

In other embodiments of the methods, haloalkylated tryptophan fluorescence arising from the protein sample is light having a wavelength of from about 400 nm to about 500 nm, said light being emitted from the protein sample when the protein sample is exposed to UV light.

Still other embodiments of the methods further comprise performing a background subtraction step. The step comprises: from the electrophoresis gel or blotting membrane comprising the protein sample, obtaining a background image, wherein the background image corresponds to a portion of the gel or membrane that contains substantially no protein; determining the total or average amount of haloalkylated tryptophan fluorescence in the background image; and subtracting the total or average amount of haloalkylated tryptophan fluorescence in the background image from the total amount of haloalkylated tryptophan fluorescence arising from the protein sample. In some of these embodiments, the background subtraction step is performed on a computer.

Also provided is a method of normalizing, using detected haloalkylated tryptophan fluorescence, the amount of protein in a first subsample of a protein sample to the amount of protein in a second subsample of the protein sample. The method comprises: quantifying the amount of haloalkylated tryptophan fluorescence detected from the first subsample; quantifying the amount of haloalkylated tryptophan fluorescence detected from the second subsample; and normalizing the amount of protein in the first subsample to the amount of protein in the second sub sample based on the amounts of haloalkylated tryptophan fluorescence detected from the first subsample and the second subsample.

In one embodiment of this method, the first subsample is one protein. In another embodiment, the second subsample is all proteins in the sample. In still another embodiment, the second subsample is a housekeeping protein. In yet another embodiment, normalizing is performed on a computer.

In another embodiment of the method, the normalizing comprises dividing the amount of haloalkylated tryptophan detected from the first subsample by the amount of haloalkylated tryptophan detected from the second subsample to obtain a ratio.

In addition, a method of comparing the relative amounts of a target protein in a first protein sample and a second protein sample is provided. The method comprises: normalizing, according to the normalizing method described above, the amount of the target protein in the first protein sample to the amount of all proteins in the first protein sample, to obtain a ratio for the first protein sample; normalizing, according to normalizing method described above, the amount of the target protein in the second protein sample to the amount of all proteins in the second protein sample, to obtain a ratio for the second protein sample; and comparing the ratios for the first and second protein samples. In this method, the first protein sample and second protein sample can be obtained from the same cell, tissue, or organism. The first protein sample and second protein sample can also be obtained from organisms of the same species.

In some embodiments, the method of normalizing a first protein subsample to a second protein subsample of a protein sample, described above, further comprises the step of obtaining an image of an electrophoresis gel or blotting membrane comprising the protein sample, and wherein the amount of haloalkylated tryptophan fluorescence detected from each subsample is quantified using the image. The image can be obtained by contacting the protein sample with a haloalkane, exposing the electrophoresis gel or blotting membrane to UV light, and recording fluorescently re-emitted light having a wavelength of from about 400 nm to about 500 nm. The haloalkane can be selected from the group consisting of chloroform, trichloroacetic acid, and trichloroethanol. The electrophoresis gel or blotting membrane can comprise a plurality of lanes, and the protein sample can occur in one lane.

In some embodiments of the normalization method, wherein an image is obtained, the amount of haloalkylated tryptophan fluorescence detected from each subsample is quantified by: designating a portion of the image to correspond to the subsample; and determining the total amount of haloalkylated tryptophan fluorescence arising from the subsample in the portion of the image. The portions of the image corresponding to the first and second subsamples can overlap.

The portion of the image corresponding to the first subsample can be of one band on the electrophoresis gel or blotting membrane, and the first subsample can be one protein. The portion of the image corresponding to the second subsample can be of an entire lane of the electrophoresis gel or blotting membrane, and the second subsample can be all proteins in the sample. Alternatively, the portion of the image corresponding to the second subsample can be of one band on the electrophoresis gel or blotting membrane, and the second subsample can be a housekeeping protein. In any embodiment, the housekeeping protein can be glyceraldehyde 3-phosphate dehydrogenase (GADPH), actin, or tubulin.

The electrophoresis gel or blotting membrane can further comprise a molecular weight standard, and the portion of the image corresponding to the first subsample or the second subsample can be designated based on molecular weight.

In one embodiment of the method, the total amount of haloalkylated tryptophan fluorescence arising from each subsample is determined by integrating the haloalkylated tryptophan fluorescence in the corresponding portion of the image over the area of that portion of the image.

In another embodiment of the method, haloalkylated tryptophan fluorescence arising from each subsample is light having a wavelength of from about 400 to about 500 nm, said light being emitted from the subsample when the subsample is exposed to UV light.

The normalization method can further comprise performing a background subtraction step. This step comprises: from the electrophoresis gel or blotting membrane comprising the protein sample, obtaining a background image, wherein the background image corresponds to a part of the gel or membrane that contains substantially no protein; determining the total or average amount of haloalkylated tryptophan fluorescence in the background image; and subtracting the total or average amount of haloalkylated tryptophan fluorescence in the background image from the total amount of haloalkylated tryptophan fluorescence in each portion of the image. The background subtraction step can be performed on a computer.

Also provided herein is a method for detecting differences in total protein contents among a plurality of biological samples from different biological sources, each sample containing about 1,000 or more distinct proteins. This method includes the following steps: (a) contacting each of said plurality of samples with a halo-substituted organic compound (i.e. haloalkane) that reacts with tryptophan residues upon irradiation with ultraviolet light to form fluorescent compounds; (b) while in contact with said halo-substituted organic compounds (i.e. haloalkanes), irradiating said samples with said ultraviolet light, and quantitatively detecting total fluorescent signals emitted from all proteins of each said sample; and (c) comparing said total fluorescent signals as an indication of differences in total protein contents among said plurality of biological samples.

In some embodiments of this method, said samples are suspended in a gel. The gel can be a polyacrylamide gel. Step (a) of the method can comprise treating the gel with said halo-substituted organic compound (i.e. haloalkane) only after said samples are suspended therein. The gel can be pre-treated by incorporation of said halo-substituted organic compound (i.e. haloalkane) therein prior to loading said plurality of samples onto the gel. Each of said samples can occupy a separate lane of the gel, and said proteins of each of said samples can be electrophoretically distributed within each of said lanes. The gel can contain said halo-substituted organic compound dissolved therein, and step (a) can comprise electrophoretically migrating all proteins of all said samples into said gel.

In other embodiments of the method of detecting differences in total protein contents among a plurality of biological samples, the samples are Western blots. The Western blots can be retained on a support selected from the group consisting of nitrocellulose, nylon, and polyvinyl difluoride. In one embodiment, the said support is a nitrocellulose membrane.

In still other embodiments of this method, said plurality of samples includes samples from different mammalian species. The plurality of samples can be serum samples, tissue homogenates, or cell lysates.

In this method, the halo-substituted organic compound (i.e. haloalkane) can be a member selected from the group consisting of chloroform, trichloroacetic acid, and trichloroethanol. The halo-substituted organic compound (i.e. haloalkane) can be a trihalo compound or trichloro compound. Alternatively, the halo-substituted organic compound (i.e. haloalkane) can be a member selected from the group consisting of trihalo aliphatic alcohols, tihalo aliphatic acids, trihaloaliphatic amines, and trihaloaliphatic alkanes.

Further provided herein is a method for correcting experimental data in comparisons between samples of protein mixtures to accommodate for differences in sample dilution, sample loading, or protein transfer inconsistencies. The method includes the steps of: (a) contacting each of said plurality of samples with a halo-substituted organic compound (i.e. haloalkane) that reacts with tryptophan residues upon irradiation with ultraviolet light to form fluorescent compounds; (b) while in contact with said halo-substituted organic compounds, irradiating said samples with said ultraviolet light, and quantitatively detecting total fluorescent signals emitted from all proteins of each said sample; and (c) normalizing said total fluorescent signals among said plurality of biological samples.

BRIEF DESCRIPTION OF THE DRAWINGS

FIGS. 1A-C show detection of haloalkylated tryptophan fluorescence from cell lysates on electrophoresis gels and blotting membranes, and correlation of fluorescence intensity with total amount of protein. (FIG. 1A) HeLa cell lysate (2.5-80 μg total protein per lane) separated by TGX "any kD" Criterion Stain-Free 1-D SDS gel (18 slots) and imaged with ChemiDoc MP. M=marker proteins. (FIG. 1B) HeLa cell lysate (2.5-80 μg total protein per lane) separated by TGX "any kD" 18 slot Criterion Stain-Free 1-D SDS gels, blotted to nitrocellulose membrane and imaged with ChemiDoc MP. M=marker proteins. (FIG. 1C) Linearity of Stain-Free technology on blotting membranes: HeLa cell lysate (2.5-80 μg total protein per lane) separated by TGX "any kD" 18 slot Criterion Stain-Free 1-D SDS gels and blotted to nitrocellulose membrane. PVDF membranes perform similarly.

FIG. 4 shows LCL cell lysates on blotting membranes visualized using haloalkylated tryptophan fluorescence and immunofluorescence. (FIG. 4, part A) LCL cell lysates (30 μg total protein per lane) separated by TGX "any kD" Criterion Stain-Free 1-D SDS gel, blotted to PVDF membrane and imaged with ChemiDoc MP. (FIG. 4, part B) Immuno-fluorescence imaging of DNA replication factor MCM7 and house-keeping protein GAPDH (serves as loading control) of LCL samples with ChemiDoc MP at different wavelengths. Monoclonal antibodies against MCM7 (mouse) and GAPDH (rabbit) were diluted 1:1000 and 1:2500 respectively. Secondary antibodies from Rockland were anti-rabbit DyLight 549 (1:10,000) and anti-mouse DyLight 649 (1:20,000).

DETAILED DESCRIPTION OF THE INVENTION

Stain-free technology is a unique in-gel chemistry whereby the gel formulation incorporates a halo-substituted organic compound, that when exposed to UV irradiation, activates a covalent reaction between the halo-substituted organic compound and tryptophan residues on the proteins in the gel, resulting in a fluorescent product and thereby permitting detection by UV-induced fluorescence. Such halo-substituted organic compounds are also referred to herein as 'haloalkanes', and the reaction of these compounds with tryptophan residues is called haloalkylation. Accordingly, a tryptophan residue is considered to be haloalkylated if it has undergone the haloalkylation reaction, and the UV-induced fluorescence of such a residue is referred to as haloalkylated tryptophan fluorescence.

It has now been discovered that the same stain-free detection technology used for individual proteins or protein mixtures from a common source can be applied to complex protein mixtures without a common origin or a common protein distribution and still achieve a valid and useful result. Thus, bulk protein quantitations of entire yet unrelated samples can be made, and the results are useful in comparing total protein amounts among the different samples, even though the protein constitution of the samples differ. Absolute quantitation can be performed by creating a standard curve using a range of known concentrations of any complex sample and evaluating the same or a different complex sample containing an unknown total amount of protein provided that the amount of protein in the complex sample is within the range of the standard curve. The applicable samples are complex biological samples that contain large numbers of proteins, as is typical of biological samples, and that have not been treated or modified in any way to alter the protein composition or distribution. The proteins in a given sample will likely therefore vary widely in the proportions of their residues that are tryptophan residues, and different samples will have different protein combinations, but all will have large numbers of different proteins, such as a thousand or more.

A variety of halo-substituted organic compounds (i.e. haloalkanes) can be used in the practice of this invention, indeed any of halo-substituted organic compound can be used that will enter into a chemical reaction with tryptophan to form a product that fluoresces upon exposure to excitation light. Halo-substituted organic compounds of particular interest are trihalo compounds, most notably trichloro compounds and those with molecular weights of 200 or less. Trihaloaliphatic alcohols, trihaloaliphatic acids, trihaloaliphatic amines, and trihaloalkanes are all useful. Specific examples are chloroform, trichloroacetic acid, and trichloroethanol. Halo-substituted organic compounds can be used individually or in combinations, such as for example combinations of two or three such compounds in approximately equal molar proportions.

Application of the halo-substituted compound (i.e. haloalkane) to the proteins can be achieved by conventional means known in the art of the use of these compounds. When the proteins are in a gel, for example, the gel can be immersed in a solution of the halo-substituted compound. The choice of solvent and the concentration of the halo-substituted compound in the solution can vary widely and can readily be optimized in terms of the intensity of the signal that is ultimately produced. Any solvent or combination of solvents that will dissolve the compound can be used. Water or mixtures of water and a lower-molecular weight alcohol such as methanol, ethanol, or isopropanol, will suffice in most cases. Concentrations may range from about 1% by weight to about 30% by weight, or in many cases from about 5% to about 20% by weight. In terms of the amount of the halo-substituted compound itself in the gel, this can vary widely as well, although effective and efficient results can generally be obtained with about 0.2% to about 2.0% of the halo-substituted compound in the gel, and in many cases from about 0.1% to about 0.5%, by volume. In some embodiments, the halo-substituted compound is added to the gel when it is poured, so that proteins come into contact with the compound when the gel is run, and no further treatment of the gel with the compound (e.g. immersing the gel in a solution of the compound) is necessary to allow the compound to react with tryptophan residues of the proteins.

The reaction times and conditions for the reaction between the proteins (i.e., their tryptophan residues) and the halo-substituted compounds can vary widely. Contact can be made at room temperature (70-75° F.), although higher and lower temperatures can also be used, provided that no additional or unwanted reactions occur at such temperatures, no phase changes occur, and the reaction occurs at an economically viable reaction rate. The contact time can likewise vary. At room temperature, effective results can generally be achieved with a contact time within the range of about thirty seconds to about thirty minutes, and in many cases optimal efficiency is achievable with a contact time of from about 1 minute to about ten minutes. When contact is achieved by immersion of a gel in a solution of the halo-substituted compound, the gel can be rinsed with water to remove excess solution following the contact time.

Once contact is made and excess halo-substituted compound removed, the reaction between the protein and the compound can be completed by irradiating the medium in which they reside with UV (ultraviolet) light of a sufficient intensity and duration to both cause the reaction to occur and to produce a fluorescent emission that can be detected and quantified. The ease of detection and quantification may vary with the type of detector used. Useful wavelengths will generally include those that reside within the range of from about 200 nm to about 400 nm, and an exposure time of from about thirty seconds to about thirty minutes, or more efficiently from about 1 minute to about ten minutes, will generally provide adequate results. Irradiation can be achieved by either transillumination or epi-illumination, and detection can be achieved by imaging such as by the use of photography, or by electronic sensors such as photodiodes, charge-coupled device (CCD) detectors, or complementary metal-oxide semiconductor (CMOS) detectors. Digital results can be analyzed by conventional imaging software. Irradiation with excitation light for purposes of detection of emissions can also be performed after the coupling reaction has occurred, either for an initial detection or for repeat detections.

The number of different proteins that will most often be present in a "complex sample" as the term is used herein will be about 50 or more, often within from about 50 to about 100,000, and in many cases from about 100 to about 50,000. The molecular weights of these proteins can vary widely, and many such samples will have molecular weights ranging from those having less than twenty amino acid residues to those having 1,000 or more, including as many as 5,000. Likewise, the number of tryptophan residues among the proteins in a single sample can range from as little as zero to as high as 5%. As noted above, examples of complex samples are serum samples, cell lysates, and tissue homogenates. Comparisons can be made between samples from different biological sources, such as different adult humans, humans of different ages, diseased and healthy humans, humans of different races or ethnicities or from different parts of the world, humans undergoing different treatments for diseases, humans undergoing treatments vs. humans not undergoing treatments, humans vs. non-human mammals, or any variable vs. a control. Other examples will be readily apparent to those of skill in the art.

In certain embodiments of this invention, the protein mixtures are suspended in gels. In other embodiments, the mixture are adhering to or otherwise suspended in or on membranes. In still others, the mixtures are adhering to or otherwise deposited on solid surfaces such as the floors or walls of sample wells. Gels in which proteins may be suspended include for example polyacrylamide gels, starch gels, and agarose gels. Of these, polyacrylamide gels are the most commonly used. Membranes on which proteins may reside are often those used in Western blots, and examples are nitrocellulose, polyvinylidene difluoride, and nylon, with nitrocellulose being the most common. Proteins suspended in gels will in many cases have been added to the gels for purposes of separation by electrophoresis within the gels, and the total protein quantitation can be performed in the gel either prior to separation or after separation. In a single gel or a single membrane, multiple samples will generally be spatially separated to allow a comparison between them, and such spatial separation can be achieved by placing the samples in different lanes of a slab gel or at the corresponding locations on a Western blot membrane to which the samples will migrate during the blotting procedure.

The halo-substituted compounds used in the practice of the present invention are preferably used in the absence of any protein stains so that the procedure is truly stain-free. By "protein stains" is meant compounds that are color-bearing or fluorescent on their own, i.e., in the absence of any reaction with amino acid residues, and that adhere to proteins by means other than a coupling reaction. Many such stains exist, examples of which, as noted above, are COOMASSIE™ Brilliant Blue, Ponceau S, and SYPRO RUBY™. However, as will be appreciated by a person having ordinary skill in the art, many of the methods described herein for protein quantification or normalization can be performed by detecting stained proteins rather than haloalkylated tryptophan fluorescence. For example, the total amount of staining in a protein sample, like the amount of detected haloalkylated tryptophan fluorescence, can be correlated with the total amount of protein in the sample for sufficiently diverse samples.

Once a protein sample of interest (herein called a target protein sample) has been reacted with a halo-substituted organic compound (i.e. a haloalkane), the sample can be further irradiated with UV light and the resulting fluorescently re-emitted light can be recorded in order to quantify the protein in the sample. If the proteins of the sample remain intermixed, such as in a test-tube, re-emitted light can be recorded using a spectrophotometer, photodiode or other similar instrument. If the proteins of the sample are physically separated from each other in an electrophoresis gel or on a blotting membrane, then re-emitted light can be recorded in an image of the gel or membrane using photographic film or a CCD camera as discussed above. Quantification can then be performed by comparing the amount of light fluorescently re-emitted by the sample (i.e., haloalkylated tryptophan fluorescence) with the amount re-emitted by one or more reference samples, where the total amount of protein in the reference sample(s) is known.

To allow direct comparison of the haloalkylated tryptophan fluorescence detected from a target protein sample and from reference protein samples, the samples can be prepared in similar ways. For example, the target and reference protein samples can be run on the same electrophoresis gel, contacted with the same haloalkane, subjected to the same source of UV light, and/or imaged using the same detection apparatus. Greater numbers of proteins in both types of samples cause differences in the tryptophan content of individual proteins to be masked, so that the overall level of haloalkylated tryptophan fluorescence from a sample better correlates with the total amount of protein. Accordingly, more accurate quantitation of a target protein sample can be performed if both the target protein sample and the reference protein samples are "complex samples" as described above. The total amount of protein in the reference sample(s) can be determined with a spectrophotometric measurement, such as a Lowry or Bradford assay, or other methods known in the art.

The amount of haloalkylated tryptophan fluorescence arising from a protein sample in an electrophoresis gel or blotting membrane can be determined by analyzing an image of the gel or membrane. In some embodiments, the image is of a portion of the gel or membrane that contains the protein sample, such as one lane of the gel or membrane. The image can analyzed using any method desired, such as by integrating or summing pixel intensity over the area of the image. Depending on how the image is acquired, haloalkylated tryptophan fluorescence may appear as a dark or light area of the image, or as an area having a certain color. Care should be taken when obtaining the image to ensure that, for as many haloalkylated proteins as possible in the sample, the amount of fluorescence recorded exceeds the minimum needed for detection but does not exceed the threshold for saturation. This helps to ensure that the total level of haloalkylated tryptophan fluorescence detected for the sample accurately reflects the total amount of protein. Without limitation, integration can be performed by designating a two-dimensional region of interest (square, rectangular, or circular, for example) in the image and summing pixel intensities within that region. Alternatively, a line can be drawn through the image (such as down the middle of a lane of the gel or membrane) to generate an intensity profile, which can be numerically integrated as a single-variable function.

In some embodiments, a background subtraction step is performed in determining the amount of haloalkylated tryptophan fluorescence arising from a protein sample. Background subtraction involves recording light in the absence of the haloalkylated protein sample, under the same or similar conditions (e.g. at the same wavelength or with the same detection apparatus) that are used when the sample is present. This light does not arise from haloalkylated tryptophan fluorescence, but rather may be ambient or may be an artifact of the detection method. The recorded light level, herein called the background light level, is then subtracted from the amount of haloalkylated tryptophan fluorescence detected for the sample. Background subtraction allows more accurate correlation of the amount of haloalkylated tryptophan fluorescence and the total amount of protein across multiple samples, by removing artifactual contributions to the amount of haloalkylated tryptophan fluorescence detected from the samples.

If the haloalkylated tryptophan fluorescence of a protein sample is measured while the sample is in a test tube, then the background light level can be determined by irradiating a different composition in a test tube with UV light and recording any re-emitted light. This composition can be a protein sample that has not been contacted with the haloalkane, the buffer in which the protein sample is suspended, or water, for example. Alternatively, if haloalkylated tryptophan fluorescence is detected for a protein sample while the sample is disposed in an electrophoresis gel or blotting membrane, then the background light level can be determined by obtaining a background image. This is an image of part of the gel or membrane that contains substantially no protein, or that contains protein that has not been contacted with the haloalkane. The background light level can then be determined by analyzing the background image as described above, by integrating any signal in the image consistent with haloalkylated tryptophan fluorescence over the area of the image. The background light level can also be the average level of tryptophan fluorescence recorded in the background image. In some embodiments, the background image is the same size as the image corresponding to one protein sample, for example the size of one lane of the gel or membrane. In other embodiments, the background image is smaller, for example corresponding to the area between two lanes. To perform background subtraction, a different background light level can be determined for every protein sample (i.e. for the target protein sample and each reference protein sample), or the same background light level can be used for more than one protein sample.

Figure 1A:
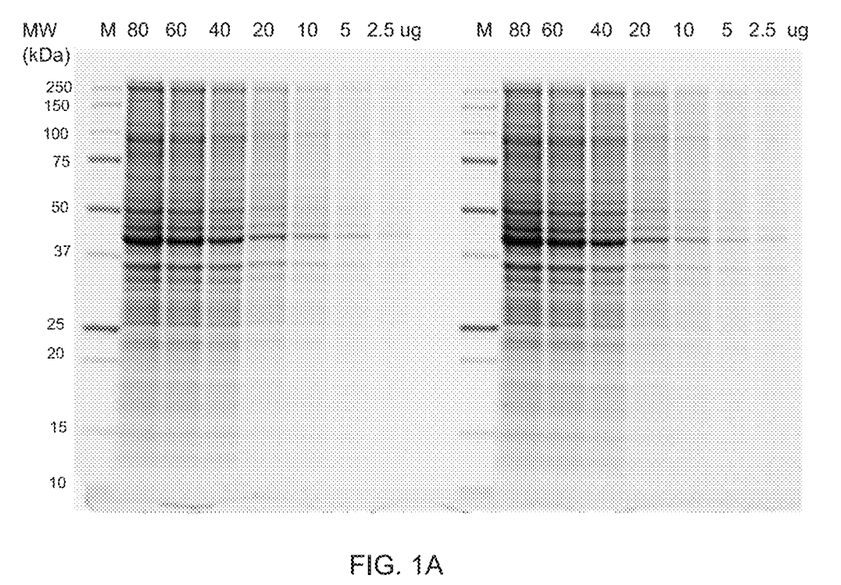
Figure 1B:
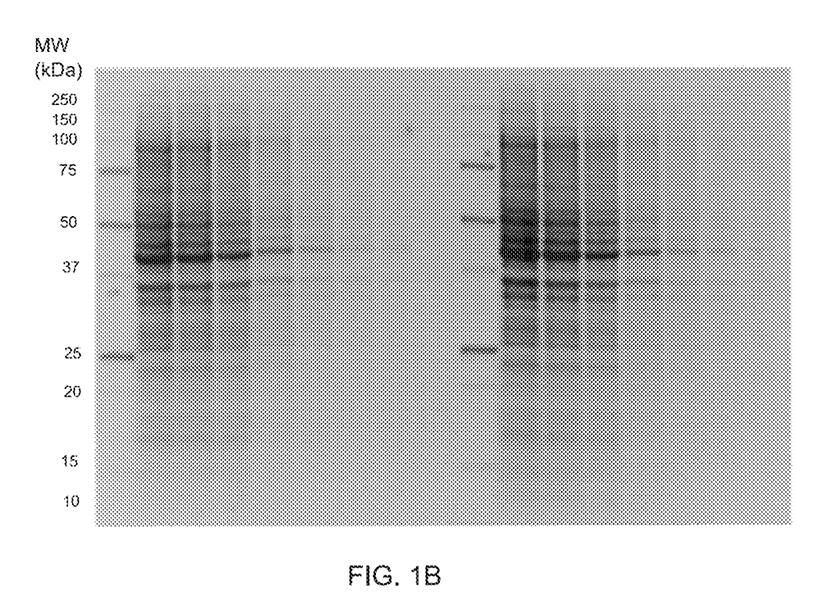
Figure 1C:
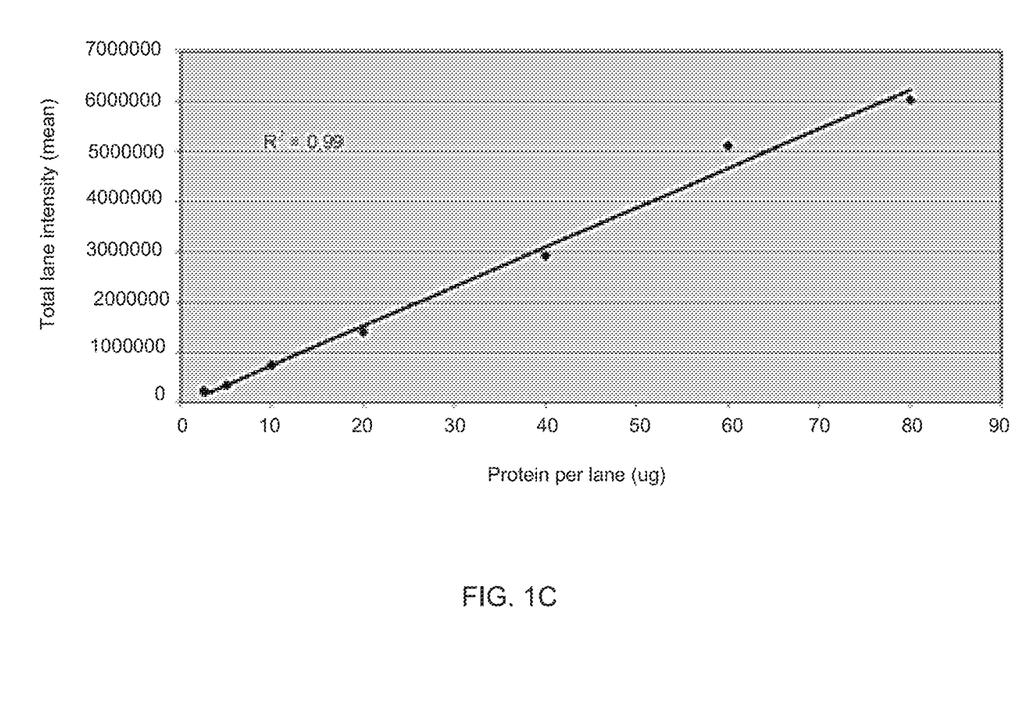

Once haloalkylated tryptophan fluorescence has been detected for the target protein sample and the reference protein samples, and the amount of haloalkylated tryptophan fluorescence for each sample has been quantified (net of any background light level), the total amount of protein in the target protein sample can be quantified. In some embodiments, this is done by constructing a standard curve, as follows. First, the amount of haloalkylated tryptophan fluorescence is plotted versus the total amount of protein for the reference protein samples (see FIG. 1). Next, an analytical function is fit to the plotted points, thereby establishing a functional relationship between the two variables being plotted. Without being bound by any theory, the fit function can be a line or any other monotonic function. Finally, the total amount of protein in the target sample is quantified from the fit function, by determining the amount of protein corresponding to the amount of haloalkylated tryptophan fluorescence detected for the target protein sample.

Figure 2:
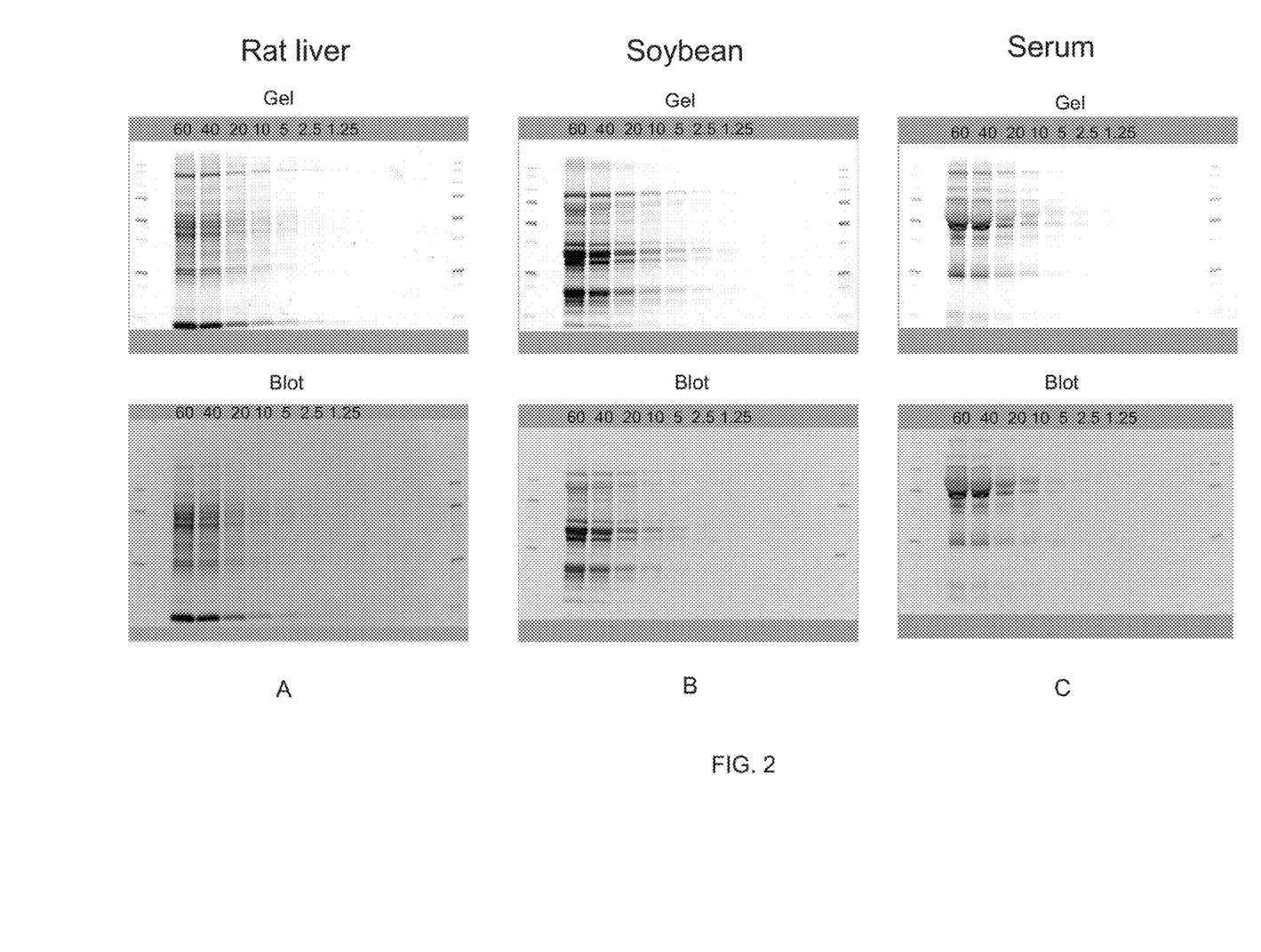
FIG. 2 shows detection of protein extracts obtained from rat liver (A), soybean (B), and human serum (C) on electrophoresis gels and blotting membranes using haloalkylated tryptophan fluorescence. The total amount of protein loaded per lane (μg) is indicated.
Figure 3:
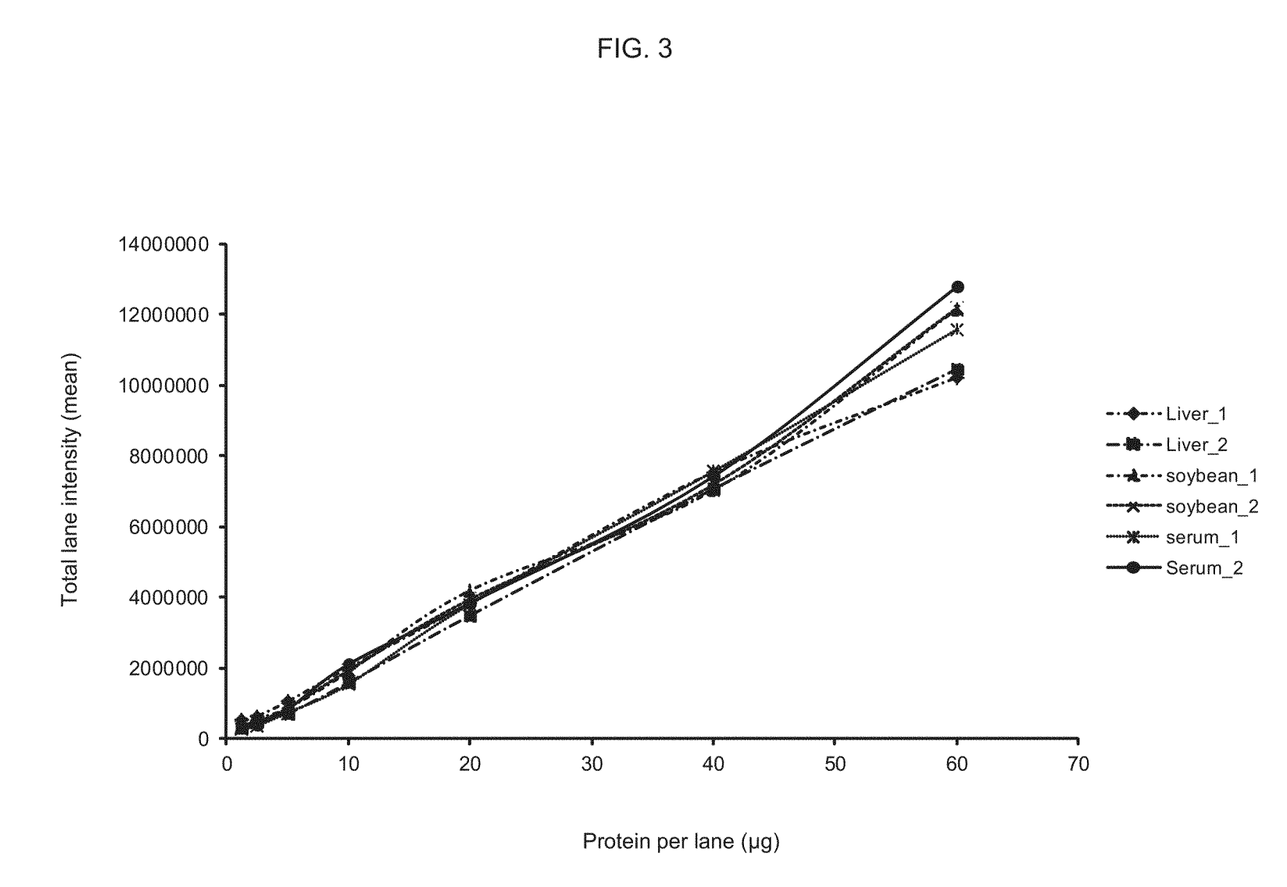
FIG. 3 shows correltion of haloalkylated tryptophan fluorescence intensity detected from samples of rat liver, soybean, and human serum proteins extracts with the total amount of protein per sample. Haloalkylated tryptophan fluorescence was quantified by obtaining images of blotting membranes such as those in FIG. 2.

In embodiments where the fit function is a line, the fitting can be performed with linear regression, for example the least squares approach. The total amount of protein in the target protein sample can be determined by linear interpolation or linear extrapolation, when the amount of haloalkylated tryptophan fluorescence detected for the target protein sample falls inside or outside (respectively) the range of values detected for the reference protein samples. The first inventors surprisingly discovered that quantitatively similar standard curves were obtained from reference protein samples having diverse origins—for example, samples obtained from different cell types or organisms (see FIGS. 2 and 3). Therefore, a new standard curve need not be constructed for every target protein sample, and the protein content of the reference protein samples need not be closely related to that of the target protein sample in order to accurately quantify the total amount of protein in the target protein sample. Rather, one standard curve can be constructed using a set of reference protein samples of any origin, provided that each of these samples has a sufficient diversity of proteins, and this curve can be used to quantify the total amount of protein in many different target protein samples.

In some embodiments of the invention, the total amount of protein in a target protein sample can be quantified or characterized without constructing a standard curve or otherwise relying upon the amounts of haloalkylated tryptophan fluorescence detected for multiple reference protein samples. For example, in some embodiments, the amounts of haloalkylated tryptophan fluorescence can be compared for a target protein sample and a single reference protein sample. If the total amount of protein in the reference protein sample is known (for example, from a spectrophotometric measurement, as discussed above), then this amount multiplied by the ratio of the amounts of haloalkylated tryptophan fluorescence for the two samples provides an estimate of the total amount of protein in the target protein sample. The accuracy of this estimate depends on the number of proteins in the target and reference protein samples, the average number of tryptophan residues in proteins of the samples, and whether background subtraction was performed, among other factors. In other embodiments, the amounts of haloalkylated tryptophan fluorescence can be compared for two target protein samples where the total amount of protein is not known for either sample. Here, the samples can be compared by calculating the ratio of the amounts of detected haloalkylated tryptophan fluorescence. This ratio can be interpreted as the ratio of the total amounts of protein, or an estimate thereof. For example, a target protein sample that emits twice as much haloalkylated tryptophan fluorescence as another sample has roughly twice as much protein, all else being equal. The accuracy of this estimate depends on a number of factors, as discussed above.

The methods described herein for quantifying the amount of haloalkylated tryptophan fluorescence detected from a protein sample can also be used to perform normalization. In some embodiments, normalization involves identifying one or more subsamples of the protein sample. A subsample is a subset of the proteins in the sample, and can be one protein, multiple proteins, or all of the proteins in the sample. A subsample can be separated from any other proteins in the sample as desired, for example on an electrophoresis gel or blotting membrane, and identified using a molecular weight standard, co-migrating dye, or the banding pattern on the gel or membrane, among other methods. Once identified, the amount of haloalkylated tryptophan fluorescence detected from a subsample can be quantified. In some embodiments, normalization comprises quantifying the amounts of haloalkylated tryptophan fluorescence detected from two different subsamples (i.e. a first subsample and a second subsample), and comparing these amounts.

Quantification can be performed using an image of an electrophoresis gel or blotting membrane as described above. The amount of haloalkylated tryptophan fluorescence detected from each subsample can be quantified by first designating a portion of the image to correspond to the subsample. This can be done by marking a region of interest in the image using software, and can be based on molecular weight, for example by making reference to a molecular weight standard in the gel or membrane that also appears in the image. In preferred embodiments, the portion of the image is coextensive with the entire subsample. Next, the total amount of haloalkylated tryptophan fluorescence arising from the subsample is determined. This determination can be made by integrating pixel intensity over the designated portion of the image, or otherwise analyzing the portion of the image as desired. In some embodiments, a background subtraction step is also performed by obtaining a background image of the gel or membrane, as discussed above, determining the background light level (e.g., the total or average amount of haloalkylated tryptophan fluorescence) associated with the background image, and subtracting the background light level from the total amount of haloalkylated tryptophan fluorescence in each designated portion of the image.

When normalization is performed using an image of electrophoresis gel or blotting membrane, the protein sample from which the first and second subsamples are drawn can occur in one lane of the gel or membrane. The portions of the image corresponding to the first subsample and the second subsample can therefore be of different parts of the same lane. In some embodiments, the first or second subsample is a single protein and the corresponding portion of the image is of a single band on the gel or membrane. In particular, the second subsample can be a housekeeping protein, and normalization can be performed with respect to the housekeeping protein as is practiced in the art with other detection technologies (e.g., antibodies). In some embodiments, the second subsample is all proteins in the sample, and so the corresponding portion of the image is of an entire lane on the gel or membrane. These embodiments facilitate total protein normalization (TPN). The first and second subsamples can indeed be chosen and identified as desired and without restriction. Accordingly, the portions of the image corresponding to the first and second subsamples can overlap.

In some embodiments, normalization comprises dividing the amount of haloalkylated tryptophan fluorescence detected from the first subsample by the amount of haloalkylated tryptophan fluorescence detected from the second subsample to obtain a ratio. In this case, the first subsample is said to be normalized to the second subsample. When the second subsample is the entire sample, then dividing the amounts of detected fluorescence this way constitutes TPN, and the ratio reflects the abundance of proteins in the first subsample with respect to all proteins in the sample. In most cases, the ratio resulting from normalization is not equal to the ratio of the total amounts of protein in the first and second subsamples, because both subsamples do not contain sufficient diversity of proteins to mask differences in tryptophan content between individual proteins. However, the normalization ratio can be compared between samples of similar origin to track differences in the relative abundances of proteins in the first and second subsamples, assuming the subsamples are identified the same way for different samples. For example, total protein normalization can be performed on a single target protein from a first protein sample and a second protein sample, and the resulting ratios can be used to compare the relative amounts of the target protein in the two samples (see FIG. 4 and Table 1). The two samples can be obtained from the same cell, tissue, or organism, or from cells, tissues, or organisms of the same species. The two samples, or the cells, tissues, or organisms from which they are derived, can be treated differently (for example, one can be subjected to a drug and one can serve as a control), and the normalized amounts of a protein in the samples can reflect the differential treatment.

Many of the methods disclosed herein can be performed on a computer or using a computer system. These methods include, without limitation: quantifying the amount of haloalkylated tryptophan fluorescence detected from a protein sample, such as in an image; integrating pixel density in an image; designating a portion of an image for analysis; performing background subtraction; otherwise manipulating or processing an image; constructing a standard curve, such as by performing linear regression; calculating a ratio; and comparing ratios. Computer algorithms for performing these methods can be encoded using programming languages and structures known to those having skill in the art, and executed on standard computer systems. Further disclosure of computer systems that may be used in embodiments of the invention is provided below.

Figure 5:
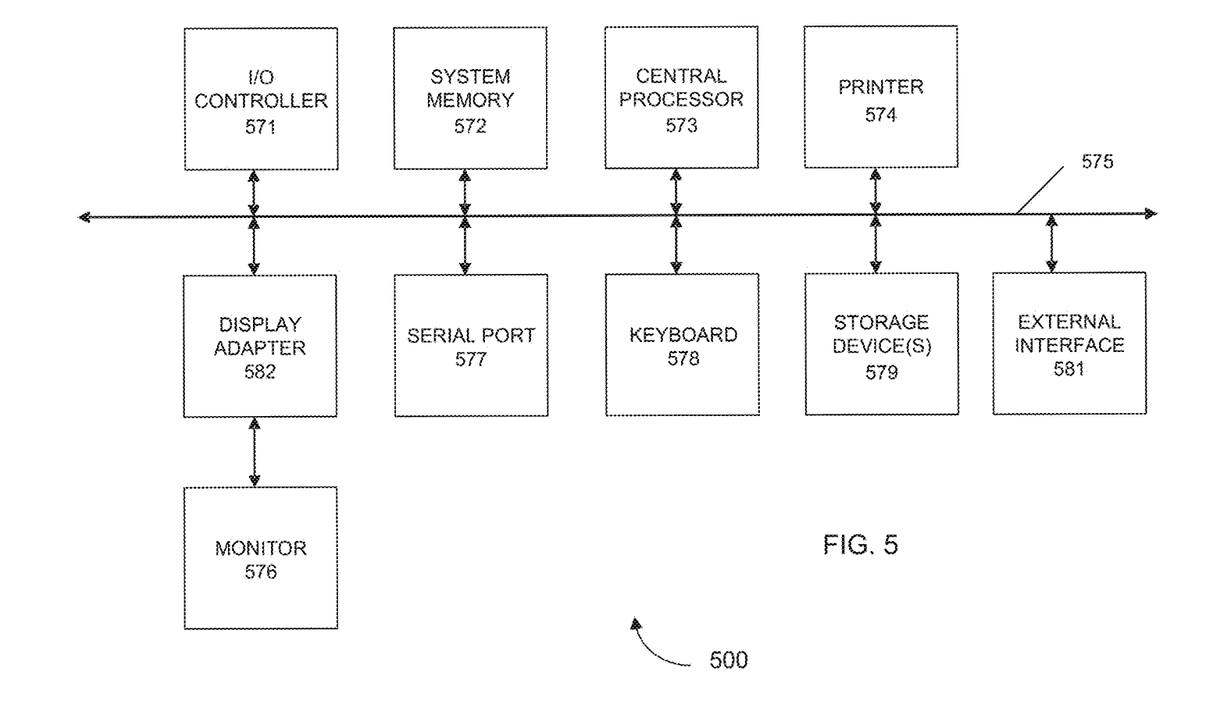
FIG. 5 shows a computer system for use with some embodiments of the invention.

Any of the computer systems mentioned herein may utilize any suitable number of subsystems. Examples of such subsystems are shown in FIG. 5 in computer apparatus 500. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 5 are interconnected via a system bus 575. Additional subsystems such as a printer 574, keyboard 578, storage device(s) 579, monitor 576, which is coupled to display adapter 582, and others are shown. Peripherals and input/output (I/O) devices, which couple to I/O controller 571, can be connected to the computer system by any number of means known in the art, such as serial port 577. For example, serial port 577 or external interface 581 (e.g. Ethernet, Wi-Fi, etc.) can be used to connect computer system 500 to a wide area network such as the Internet, a mouse input device, or a scanner. The interconnection via system bus 575 allows the central processor 573 to communicate with each subsystem and to control the execution of instructions from system memory 572 or the storage device(s) 579 (e.g., a fixed disk, such as a hard drive or optical disk), as well as the exchange of information between subsystems. The system memory 572 and/or the storage device(s) 579 may embody a computer readable medium. Any of the data mentioned herein can be output from one component to another component and can be output to the user.

A computer system can include a plurality of the same components or subsystems, e.g., connected together by external interface 581 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that some of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

The methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

Example 1: Correlation of Haloalkylated Tryptophan Fluorescence Intensity with Cell Lysate Total Protein Quantity Stain-free technology enables fluorescent visualization of SDS PAGE gels and corresponding blots. FIG. 1A shows an electropherogram of HeLa cell lysate (2.5-80 μg total protein per lane) separated by TGX "any kD" Criterion Stain-Free 1-D SDS gel (18 slots) and imaged with ChemiDoc MP, where the M lane designates the marker proteins. FIG. 1B shows a Western blot of the same cell lysate separated in the same gels with the same lane loadings, the blot being on a nitrocellulose membrane and imaged with ChemiDoc MP, where the M lane again represents the marker proteins. The quality of SDS-PAGE separations before blotting can be easily monitored and the transfer efficiency of the blotting process can be quickly inspected by imaging both the membrane (see FIG. 1B) and the SDS gel after the blotting process. The relative amount of total protein in each lane on the blot can be calculated and used for quantitation normalization.

Stain-free technology offers comparable sensitivity to conventional blot stains such as SYPRO Ruby and Ponceau S, and provides better reproducibility and linearity. FIG. 1C, which is a plot of the total lane intensity (mean value) vs. the of protein per lane, taken from FIG. 1B, shows that the linear range of the stain-free technology extends up to 80 μg protein for 18 wells. The linear range can extend further to 110 μg per lane for 12-well mid-size gels (data not shown). These ranges fit well with usual protein loads in quantitative Western blotting experiments and enable loading control calculations over a wide protein loading range.

Example 2: Invariance of Total Haloalkylated Tryptophan Fluorescence with Origin and Composition of Protein Extract To determine whether the source and composition of a diverse mixture of proteins significantly affects the total amount of haloalkylated tryptophan fluorescence detected from the mixture, protein extracts were obtained from different organisms. The extracts were then diluted to known concentrations to obtain reference protein samples, which were detected on blotting membranes following haloalkylation. The total amount of haloalkylated tryptophan fluorescence detected from each sample was correlated with the total amount of protein in the sample.

Protein extracts were obtained from rat liver, soybean, and human serum, and the concentration of protein in each extract was determined using established spectrophotometric methods. Reference protein samples prepared from the extracts (60, 40, 20, 10, 5, 2.5, 1.25 μg) were loaded in duplicate onto Criterion TGX 12-2 well "any kD" polyacrylamide gels (Bio-Rad) and separated using electrophoresis. The samples from each gel were then transferred to a nitrocellulose membrane using the Trans-Blot Turbo system (Bio-Rad). Haloalkylated tryptophan fluorescence was imaged before and after transfer (FIG. 2) using the Gel Doc EZ system (Bio-Rad). Gel and membrane images showed different distributions of protein molecular weights for the different protein extracts.

Images of the membranes were analyzed to quantify the total haloalkylated tryptophan fluorescence from each lane. Analysis was performed using the "bands and lanes" tool in ImageLab software. Plots of total fluorescence intensity versus the total amount of protein (FIG. 3) were largely the same for all reference protein samples, regardless of the organism from which the samples originated.

Example 3: Western Blot Analysis with Stain-Free Technology Validates Semi-Quantitative Protein Profiling Studies Proteomic technologies like 2-D PAGE are customarily used in semi-quantitative protein profiling studies. After identifying and characterizing proteins that are expressed in different amounts by mass spectrometry, the quantitative data needs to be confirmed by a second, independent method like Western blotting.

The effect of γ-irradiation on a human LCL cell line (lymphoblastoid cell line) was studied by 2-D PAGE. Among many other proteins that were expressed in different amounts, MCM7, a DNA replication factor, was identified to be down-regulated by about a factor of two in the irradiated LCL sample as compared to a non-irradiated control. To validate this result, a quantitative Western blotting experiment was performed with monoclonal antibodies raised against MCM7. Two data normalization methods, namely data normalization with the GAPDH HKP and the stain-free technology of the present invention, were applied and compared.

Figure 4:
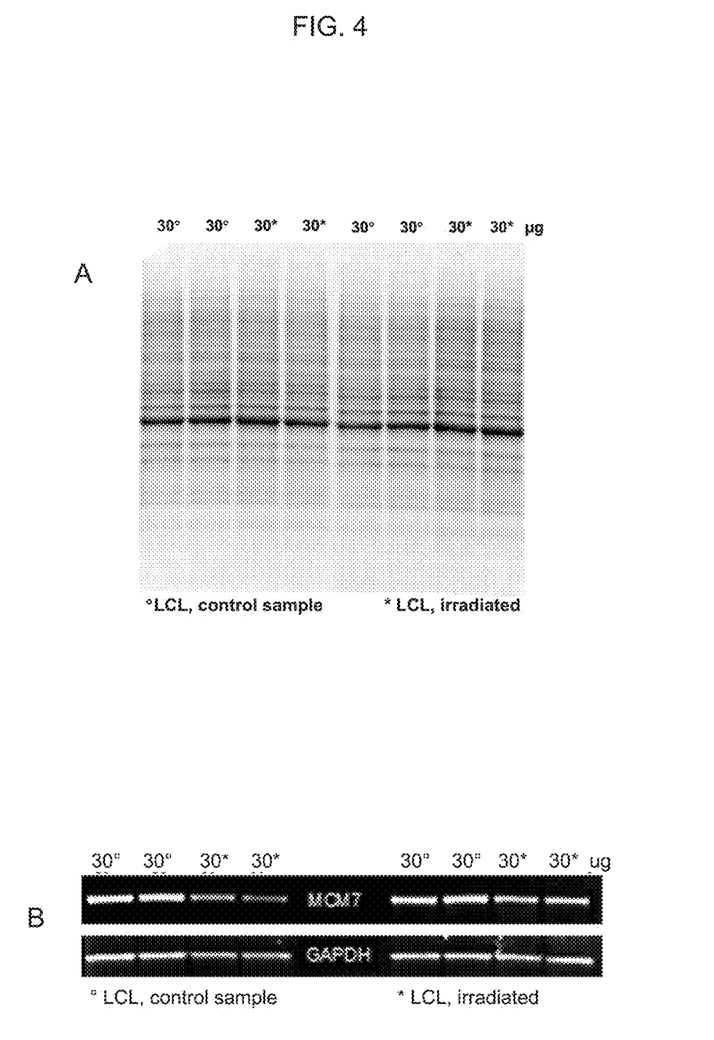

FIG. 4, part A represents LCL cell lysates (30 μg total protein per lane) separated by TGX "any kD" Criterion Stain-Free 1-D SDS gel, blotted to PVDF membrane and imaged with ChemiDoc MP, and shows the corresponding high quality PVDF (polyvinylidene difluoride) blot of the LCL samples before antibody incubation, comparing the control samples (identified by the degree sign) with the irradiated samples (identified by the asterisk). FIG. 4, part B represents Immuno-fluorescence imaging of DNA replication factor MCM7 and house-keeping protein GAPDH (serves as loading control) of LCL samples with ChemiDoc MP at different wavelengths. Monoclonal antibodies against MCM7 (mouse) and GAPDH (rabbit) were diluted 1:1000 and 1:2500 respectively. Secondary antibodies from Rockland were anti-rabbit DyLight 549 (1:10,000) and anti-mouse DyLight 649 (1:20,000). FIG. 4, part B thus illustrates probing the same PVDF blot for target protein MCM7 and loading control protein GAPDH using a multiplex fluorescent approach. By running a dilution series of the LCL samples from 10-50 μg per lane, it was verified beforehand that the 30 μg protein load in combination with the antibody dilutions as described in FIG. 4, part B give linear fluorescent signals (data not shown).

Data normalization of the MCM7 signal intensities with GAPDH data and Stain Free data (see Table 1) revealed that the down-regulation factors of MCM7 are 0.59 with GAPDH (p-value <0.03) and 0.44 with Stain-Free (p-value <0.008). Both factors reflect well with the expected down-regulation of about 50% initially obtained from 2-D PAGE experiments. The comparison of raw MCM7 signals (no normalization) reveals a down-regulation factor of 0.48 (p-value <0.02) with 35% standard deviation. Although both normalization methods were successful in achieving normalization, the stain-free technology of the present invention did not require method optimization, had fewer operative steps to perform, took less time to get results, and allowed tracking of proteins from the gel to the blot.

MCM7 was identified by 2-D PAGE to be down-regulated by about 50% and this result can be confirmed by Western-Blotting. Data normalization with Stain-Free technology revealed a deregulation factor of 0.44, GAPDH normalization of 0.59.

TABLE 1

Normalization of MCM7 (DNA replication factor) signals of Figure 4b with Stain-Free data from Figure 2a and GAPDH signals of Figure 4b.

| µg protein per lane | SF, total lane intensity control | MCM7 signal control | Normalization: MCM7/SF control | SF, total lane intensity irradiated | MCM7 signal irradiated | Normalization: MCM7/SF irradiated |
|---|---|---|---|---|---|---|
| 30 | 6,249,312 | 373,374,161 | 59.75 | 6,288,479 | 142,321,333 | 22.63 |
| 30 | 6,597,084 | 330,590,416 | 50.11 | 5,751,644 | 95,449,064 | 16.60 |
| 30 | 5,778,980 | 247,831,492 | 42.88 | 6,776,037 | 158,951,514 | 23.46 |
| 30 | 6,282,159 | 287,348,860 | 45.74 | 7,047,180 | 170,342,314 | 24.17 |
|  | 6,226,884 mean | 309786232 mean | 49.62 mean | 6,465,835 mean | 141766056 mean | 21.71 mean |
|  | 5.4 standard deviation (%) | 17.5 standard deviation (%) | 14.9 standard deviation (%) | 8.8 standard deviation (%) | 23.2 standard deviation (%) | 16.0 standard deviation (%) |
|  colspan | | | Estimation of MCM7 down-regulation: 21.7/49.6 = 0.44 | | | |

| µg protein per lane | GAPDH signal control | MCM7 signal control | Normalization: MCM7/GAPDH control | GAPDH signal irradiated | MCM7 signal irradiated | Normalization: MCM7/GAPDH irradiated |
|---|---|---|---|---|---|---|
| 30 | 276,574,305 | 373,374,161 | 1.35 | 144,301,840 | 142,321,333 | 0.99 |
| 30 | 203,414,378 | 330,590,416 | 1.63 | 150,089,223 | 95,449,064 | 0.64 |
| 30 | 189,193,277 | 247,831,492 | 1.31 | 159,867,394 | 158,951,514 | 0.99 |
| 30 | 187,281,443 | 287,348,860 | 1.53 | 207,153,651 | 170,342,314 | 0.82 |
|  | 214115851 mean | 309786232 mean | 1.45 mean | 165353027 mean | 141766056 mean | 0.86 mean |
|  | 19.7 standard deviation (%) | 17.5 standard deviation (%) | 10.3 standard deviation (%) | 17.3 standard deviation (%) | 23.2 standard deviation (%) | 19.6 standard deviation (%) |
|  | | | Estimation of MCM7 down-regulation 0.86/1.45 = 0.59 | | | |

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method of normalizing, using detected haloalkylated tryptophan fluorescence, the amount of protein in a first subsample of a protein sample to the amount of protein in a second subsample of the protein sample, the method comprising:
    quantifying the amount of haloalkylated tryptophan fluorescence detected from the first subsample;
    quantifying the amount of haloalkylated tryptophan fluorescence detected from the second subsample, wherein the second subsample comprises 50 or more proteins; and
    normalizing the amount of protein in the first subsample to the amount of protein in the second subsample based on the amounts of haloalkylated tryptophan fluorescence detected from the first subsample and the second subsample.

2. The method of claim 1, wherein the first subsample is one protein.

3. The method of claim 1, wherein the second subsample is all proteins in the sample.

4. The method of claim 1, wherein said normalizing is performed on a computer.

5. The method of claim 1, wherein said normalizing comprises dividing the amount of haloalkylated tryptophan detected from the first subsample by the amount of haloalkylated tryptophan detected from the second subsample to obtain a ratio.

6. A method of comparing the relative amounts of a target protein in a first protein sample and a second protein sample, the method comprising
    normalizing, according to claim 5, the amount of the target protein in the first protein sample to the amount of all proteins in the first protein sample, to obtain a ratio for the first protein sample;
    normalizing, according to claim 5, the amount of the target protein in the second protein sample to the amount of all proteins in the second protein sample, to obtain a ratio for the second protein sample; and
    comparing the ratios for the first and second protein samples, wherein all proteins in the first protein sample are 50 or more proteins and all proteins in the second protein sample are 50 or more proteins.

7. The method of claim 1, further comprising the step of obtaining an image of an electrophoresis gel or blotting membrane comprising the protein sample, and wherein the amount of haloalkylated tryptophan fluorescence detected from each subsample is quantified using the image.

8. The method of claim 7, wherein the image is obtained by contacting the protein sample with a haloalkane, exposing the electrophoresis gel or blotting membrane to UV light, and recording fluorescently re-emitted light having a wavelength of from about 400 nm to about 500 nm.

9. The method of claim 7, wherein the amount of haloalkylated tryptophan fluorescence detected from each subsample is quantified by:
    designating a portion of the image to correspond to the subsample; and
    determining the total amount of haloalkylated tryptophan fluorescence arising from the subsample in the portion of the image.

10. The method of claim 9, wherein the total amount of haloalkylated tryptophan fluorescence arising from each subsample is determined by integrating the haloalkylated tryptophan fluorescence in the corresponding portion of the image over the area of that portion of the image.

11. The method of claim 9, further comprising performing a background subtraction step comprising:
    from the electrophoresis gel or blotting membrane comprising the protein sample, obtaining a background image, wherein the background image corresponds to a part of the gel or membrane that contains substantially no protein;
    determining the total or average amount of haloalkylated tryptophan fluorescence in the background image; and
    subtracting the total or average amount of haloalkylated tryptophan fluorescence in the background image from the total amount of haloalkylated tryptophan fluorescence in each portion of the image.

* * * * *